(12) United States Patent
Peters

(10) Patent No.: US 8,591,107 B2
(45) Date of Patent: Nov. 26, 2013

(54) STAND FOR AN X-RAY EXAMINATION APPARATUS

(75) Inventor: Joseph Hubertus Peters, Nuenen (NL)

(73) Assignee: Koninklijke Philips N.V., Eindhoven (NL)

( * ) Notice: Subject to any disclaimer, the term of this patent is extended or adjusted under 35 U.S.C. 154(b) by 321 days.

(21) Appl. No.: 13/142,026

(22) PCT Filed: Jan. 8, 2010

(86) PCT No.: PCT/IB2010/050064
§ 371 (c)(1),
(2), (4) Date: Jul. 18, 2011

(87) PCT Pub. No.: WO2010/082147
PCT Pub. Date: Jul. 22, 2010

(65) Prior Publication Data
US 2011/0268254 A1  Nov. 3, 2011

(30) Foreign Application Priority Data

Jan. 13, 2009 (EP) .................................... 09150435

(51) Int. Cl.
*H05G 1/02* (2006.01)
(52) U.S. Cl.
USPC .......................... 378/196; 378/193; 378/197
(58) Field of Classification Search
USPC .......................... 378/193–198, 204, 205, 210
See application file for complete search history.

(56) References Cited

U.S. PATENT DOCUMENTS

| 4,024,401 | A | 5/1977 | Bernstein et al. |
| 5,050,204 | A | 9/1991 | Siczek et al. |
| 5,901,200 | A | 5/1999 | Krause |
| 6,131,690 | A | 10/2000 | Galando et al. |
| 6,431,751 | B1 | 8/2002 | Everett et al. |

FOREIGN PATENT DOCUMENTS

| DE | 3615633 | 11/1987 |
| DE | 4214087 | 5/1993 |
| JP | 2007222412 A | 9/2007 |

*Primary Examiner* — Anastasia Midkiff

(57) ABSTRACT

A stand for an X-ray examination apparatus like a C-arm (4) is proposed. The stand comprises a movable ceiling support assembly for a ceiling of a room, a ground support assembly for a floor of the room and a holder (16) extending from the ceiling support assembly to the ground support assembly. The ceiling support assembly is distanced laterally from the ground support assembly and the holder comprises a mount (30) for holding the X-ray examination apparatus above the ground support assembly. Provision of a holder between a ground support assembly and a ceiling support assembly allows to position the ceiling-rail at a distance to a patient's area where the C-arm is employed. Therefore, no dust and debris from a ceiling-rail is released over the patient's area and a sterile air flow from a ceiling is not disturbed. By pivoting the stand through a pivot bearing (14) the C-arm can be easily brought into a parking position where it does not obstruct the patient's area.

14 Claims, 4 Drawing Sheets

STAND FOR AN X-RAY EXAMINATION APPARATUS

FIELD OF THE INVENTION

The present invention relates to a stand for an X-ray examination apparatus for positioning the X-ray apparatus relative to a patient-support table. The invention further relates to an X-ray apparatus with such a stand.

BACKGROUND OF THE INVENTION

In traditional open surgery applications, X-ray imaging is often performed by relatively low-weight mobile X-ray examination apparatuses that can be positioned manually relative to a patient-support table in an operating room. Since providing X-ray images is only needed infrequently, it is useful to park the X-ray system outside of the operating area when it is not needed momentarily. In this context "park" stands for moving the X-ray apparatus fully away from the patient-support table, so that it neither disturbs the surgery nor personnel around the patient-support table.

It is a trend to replace or enhance traditional open surgery by hybrid surgical applications, wherein minimal-invasive procedures, e.g. like in interventional cardio-vascular catheterisation applications are used. For example, in a so-called AAA procedure, the abdominal aortic aneurysm is treated by the placement of multiple stents, introduced via small incisions in the patients' groin. For those procedures it is beneficial to enhance the X-ray image quality. This can be realised in using fixed X-ray examination apparatuses that often have better image quality than mobile apparatuses. Fixed X-ray apparatuses may be either floor-mounted with a stand near the patient-support table or via a ceiling-rail that is located over the patient-support table.

In U.S. Pat. No. 6,431,751 B1 a diagnostic imaging system with a C-arm is shown, that permits the C-arm to be removably attached to different ceiling-mounted support structures and to a mobile cart for mobile C-arm imaging applications.

SUMMARY OF THE INVENTION

Floor-mounted stands for X-ray examination apparatuses in general may occupy floor-space in or very near an operating area leading to inconvenient characteristics for parking the apparatus and cleaning the floor. Therefore, ceiling-rail-mounted systems may be preferred in hybrid surgery. Commonly, the ceiling rail is situated directly above the patient-support table and easily allows moving heavy C-arms or the like. Due to the position above the patient-support table it may be possible that dust and debris can be released from the ceiling rail if it is not cleaned properly. In case provisions for sterile airflow are installed above the patient-support table, the rails may also disturb a desired laminar flow pattern. Using two separate ceiling rails that are distanced from each other might be a solution to not disturb the sterile airflow but also might complicate positioning other equipment like surgical lights, suspended equipment carriers, booms delivering medical gases, etc. on the ceiling due to larger occupied ceiling space. Additionally it might be possible to mount a C-arm of an X-ray examination apparatus on a stand realised as a ceiling-suspended arm with multiple flexible joints that neither obstructs floor space nor occupies ceiling space. Such a suspended arm must be very robust and thus heavy and needs a very rigid ceiling construction in order to prevent mechanical resonance or other potential disturbance or damage.

In case a ceiling-rail mounted X-ray examination apparatus is temporarily not needed, it is moved along the ceiling rail to a parking position, which may be problematic because areas in longitudinal direction, either towards foot- or head-end is often occupied by other surgical equipment, e.g. sterile instruments and anaesthetics.

Accordingly, there may be a need for a stand for an X-ray examination apparatus which may allow to overcome at least some of the above insufficiencies. Particularly, there may be a need for such a stand that does not use a ceiling-rail which disturbs a sterile airflow or releases dust and debris into a patient's area. Additionally there may be a need for a stand that may be brought into a parking position in the operating room easily, wherein in the parking position the X-ray examination apparatus does not obstruct floor space around a patient-support table and that does not need a highly robust ceiling construction.

These needs may be met by the subject-matter according to the first independent claim. Various embodiments of the present invention are described in the dependent claims.

According to a first aspect of the present invention, a stand for an X-ray examination apparatus is proposed. Therein, the stand comprises a ceiling support assembly, a movable ground support assembly and a holder which is positioned between and attached to the ceiling support assembly and the ground support assembly, wherein the ceiling support assembly is distanced laterally from the ground support assembly.

In the following description of the invention the expression "C-arm" is used often, which is a main component of an X-ray examination apparatus and mainly encompasses an X-ray source and an X-ray detector positioned opposite to each other in a C-shaped frame. Besides that, the X-ray examination apparatus also comprises a table and a stand for holding the C-arm at desired positions relative to the table. Other components like post-processing software, viewing monitors, control devices and the such are not relevant for presenting the invention.

A gist of the present invention may be seen as being based on the following ideas:

A movable ground support assembly is provided to carry a main part of the weight of a C-arm or the like of an X-ray examination apparatus. Such a ground support may be realised by any rolling, sliding or gliding means, for example a carriage, one or more rollers or wheels with a fixed or variable direction of motion along a floor. A benefit of the proposed stand is that the ground support assembly itself does not necessarily need to be statically defined due to the ceiling support assembly which guides and levels the ground support assembly motion. For this purpose a holder extending from the ceiling support assembly to the ground support assembly is provided. This results in the ground support assembly following the motion of the ceiling support assembly. The stand functions are thus separated into different components—the ground support assembly merely acts as a provision to carry the weight of the C-arm whereby the ceiling support assembly is used for guiding the motion of the stand. For this reason, the ceiling support assembly does not need to be constructed rigidly and thus does not need a heavy ceiling construction.

Basically the holder may be of any shape that may be suitable for the purpose of guiding a motion and leveling the C-arm. The holder may be straight and be designed as a beam, a frame, a rod or the like with an appropriate profile to be suited for accommodating the C-arm. It is not necessary that the profile of the holder is constant over its whole length. It may be adapted for an improved load introduction capability in an area where the C-arm is attached to the holder. In general, the profile of the holder can be of any kind, like a double-T-profile, a U-profile, a substantially rectangular or circular profile, etc. to which the subject-matter of the present invention is not limited. It is pointed out that for usage in sterile operating rooms it may be beneficial to design the profile for optimal cleaning ability so that recesses or undercuts are reduced to a minimum or completely eliminated so that no accumulation of dust, debris or dirt in general is possible. This could be realized as a profile with a closed and smooth circumferential area.

Furthermore, the holder can have any other non straight shape, if the desired shape still permits to accommodate the C-arm and does not obstruct people or objects in the operating room. For example, the holder may comprise an optimized shape regarding accidental head contact and may be S-shaped or may comprise multiple straight sections that are connected to each other.

The holder shall comprise at least one appropriate joint or fitting for carrying the C-arm or the like of an X-ray examination apparatus. This joint shall be able to hold the C-arm in a stable and definite position relative to a patient-support table. It may also be beneficial that the joint allows a pivoting motion of the C-arm so that an imaging angle can be adjusted. Favorably the joint for holding the C-arm is positioned in such a way that the center of gravity of the C-arm is positioned as close as possible above the ground support assembly. This increases the part of the C-arm weight to be carried by the ground support assembly so that the ceiling-rail assembly is even less loaded.

The stand proposed herein is considered in a stable state when ceiling support assembly and the movable ground support assembly are positioned at a lateral distance relative to each other, highly reducing bending and resonance effects of the holder. In a state where the C-arm is positioned at a patient-support table also the ground support assembly is in an area nearby the patient-support table. Therefore, due to the lateral distance, the ceiling support assembly is distanced from the patient's area. The danger of releasing dust and debris into the patient's area is thus highly reduced. Also, outlets for sterile airflow are not disturbed and can be optimally placed above the patient-support table.

Moving the X-ray examination apparatus between the patient's area and a parking position may be achieved by pivoting the stand around a vertical axis relative to the ceiling, wherein the vertical axis may be positioned in the ceiling support assembly. For instance, in a first pivot position the C-arm may reach the patient-support table and allows X-ray imaging of the patient. In a second pivot position, which can be reached by pivoting the stand about 90° or more around the vertical axis, the C-arm may be moved away from the patient-support table. Therefore it is beneficial to choose a lateral distance between the ceiling support assembly and the patient-support table that allows reaching imaging and parking positions by pivoting the stand. Increasing the distance between the ceiling support assembly and the ground support assembly increases the distance of the patient-support table to the parking area of the C-arm. In pivoting the whole stand according to the present invention the C-arm may be parked in a position where it does not obstruct persons, devices or surgical instruments arranged at the foot-end or the head-end of the patient-support table. Also, since there is no floor-mounted provision with a fixed position to hold the C-arm, the operation room can be cleaned more efficiently.

The use of such a stand may have a number of desired effects. Firstly, the holder for holding the C-arm is supported by two provisions that may prevent a single ceiling- or ground-mounted support to be overly rigid and large.

Another desired effect can be seen in the fact that according to the above description a ceiling support assembly can be positioned at a lateral distance to a patient's area. In case the ceiling support assembly is not cleaned properly or regularly and dust and debris is released it does not fall directly onto the patient-support table. This highly improves the sterility of the operation area.

Additionally, another desired effect may be that a laminar airflow from a sterile air source is not disturbed by one or more ceiling support assemblies so that the stand according to the invention leads to an improved ventilation in the patient area.

In the following, possible features and desired effects of embodiments of the proposed stand for an X-ray examination apparatus will be described.

The stand proposed herein may comprise at least one ceiling-rail assembly as a ceiling support assembly which is attached to the ceiling of the operating room. The ceiling-rail assembly may also be integrated into the ceiling leaving only a slot through which the holder may extend to wheels or rollers running within the ceiling-rail.

The ceiling-rail may comprise at least one longitudinal ceiling-rail section. In this context, longitudinal stands for being substantially parallel to a longitudinal side of a patient-support table that allows positioning of the C-arm along the longitudinal side of the patient-support table.

According to a further embodiment of the present invention, the ceiling-rail assembly may also include a lateral ceiling-rail section. Analog to the longitudinal ceiling-rail section described above, the lateral ceiling-rail is substantially parallel to a lateral side of the patient-support table. Generally, the lateral ceiling-rail may be arranged perpendicular to the longitudinal ceiling-rail. The lateral ceiling-rail enables a lateral displacement of the C-arm examination apparatus.

Additionally, the ceiling support assembly may comprise at least two ceiling-rails wherein one of the ceiling rails is arranged perpendicular to at least one remaining ceiling-rail. At least two carriages are used for moving along the ceiling rails, one for each direction. Thereby a lateral and a longitudinal motion can be realized and the ceiling-rail may be of a single longitudinal ceiling-rail section.

According to another embodiment of the present invention, the ceiling-rail assembly comprises at least one pivot bearing assembly. This provides for the ability to pivot the stand according to the invention around a vertical axis that is defined by the pivot bearing. Pivoting the stand into a first position brings the stand and the C-arm into a parking position. Pivoting the stand about 90° or more leads to a second pivot position, in which the C-arm is positioned at the patient-support table in order to be ready for X-ray imaging of a patient on the table. In the parking position, the C-arm does not obstruct the patient-support table neither at the foot- and nor at the head-end.

It is preferred that the pivot bearing can be locked. This prevents the holder and the ground support assembly to leave their defined position. It may be helpful to activate and release the pivot bearing lock electrically, pneumatically or manually through a lever or through a Bowden cable.

In another embodiment of the present invention a carriage is movably supported free of play on the ceiling-rail. The carriage may include wheels or rollers that limit the spatial degree of freedom of the carriage to a motion in forward or backward direction on the ceiling-rail.

It may be beneficial to mount the holder on the carriage firmly so that it cannot be tilted or turned relative to the carriage. In case a pivot bearing is included into the stand the holder shall not be able to tilt or rotate while the pivot bearing is locked or deactivated. This improves the stability of the stand and prevents the ground support assembly to follow the ceiling support assembly imprecisely.

In a still further embodiment of the present invention the movement along the ceiling-support assembly can be locked by means of a brake. This improves the ability to pivot the stand into or from a parking position. The brake may be activated and released electrically, pneumatically or manually. If the C-arm needs to be brought into a parking position the brake may be activated by pressing a button. Additionally, a pivot bearing is unlocked at the same time so the stand can be easily pivoted around the pivot bearing and the C-arm is moved away from the patient-support table.

It is preferred to position the ground support assembly as close as possible near the center of gravity of the C-arm plus holder. This reduces the part of the weight that the holder has to carry. A carriage on the ceiling rail will be easier to move and the ceiling-rail itself can be realized with smaller dimensions than ceiling-rails for C-arms in prior art.

According to a still further embodiment of the present invention, the ground support assembly includes at least one wheel. The wheel is designed in a manner to provide a support for the total weight force of the C-arm and the holder. It may be even more beneficial to include two wheels arranged in parallel into the ground support assembly, preferably with two wheel bearings for enabling the wheels to turn independently. These two wheels can be designed more narrow than a single wheel, because they share the C-arm weight. More narrow wheels may reduce the friction of the wheels when it is needed to turn them around a vertical axis so the stand according to the invention may move around corners with two wheels easier than with a single wheel.

In a still further embodiment of the present invention the ground support assembly includes at least one pivot bearing for turning the at least one wheel or other support means around a vertical axis. This leads to an extended movability to follow a predetermined motion along the ceiling support assembly and for moving into and from a parking position.

In another further embodiment of the present invention wheels included in the ground support assembly are motorized. Since the C-arm is heavy, a motor may provide for an improved handling of the C-arm particularly when it is not used frequently during an operation. The motor may be controlled through a control device and may automatically move the stand to a parking position or to the patient-support table. Alternately the motor can be activated manually by pressing forward or reverse buttons on an input device or the like. As another alternative the motor supports a manual movement of the holder so that it is turned on when a wheel motion is detected and is turned off when the holder is not moved manually any more.

The needs for a stand for an X-ray examination apparatus may also be met by the subject-matter according to the second independent claim, which is directed to an X-ray examination apparatus including a stand according to the present invention.

It has to be noted that features and desired effects of the present invention have been described with reference to different embodiments of the invention. However, a person skilled in the art will gather from the above and the following description that, unless other notified, in addition to any combination or features belonging to one embodiment also any combinations between features relating to different embodiments or to a manufacturing method is considered to be disclosed with this application.

BRIEF DESCRIPTION OF THE DRAWINGS

Features and desired effects of the present invention will be further described with respect to specific embodiments as shown in the accompanying figures but to which the invention shall not limited. The drawings in the figures are only schematically and not to scale. Similar elements in the figures are referred to with similar reference signs.

DETAILED DESCRIPTION OF PREFERRED EMBODIMENTS

Figure 1:
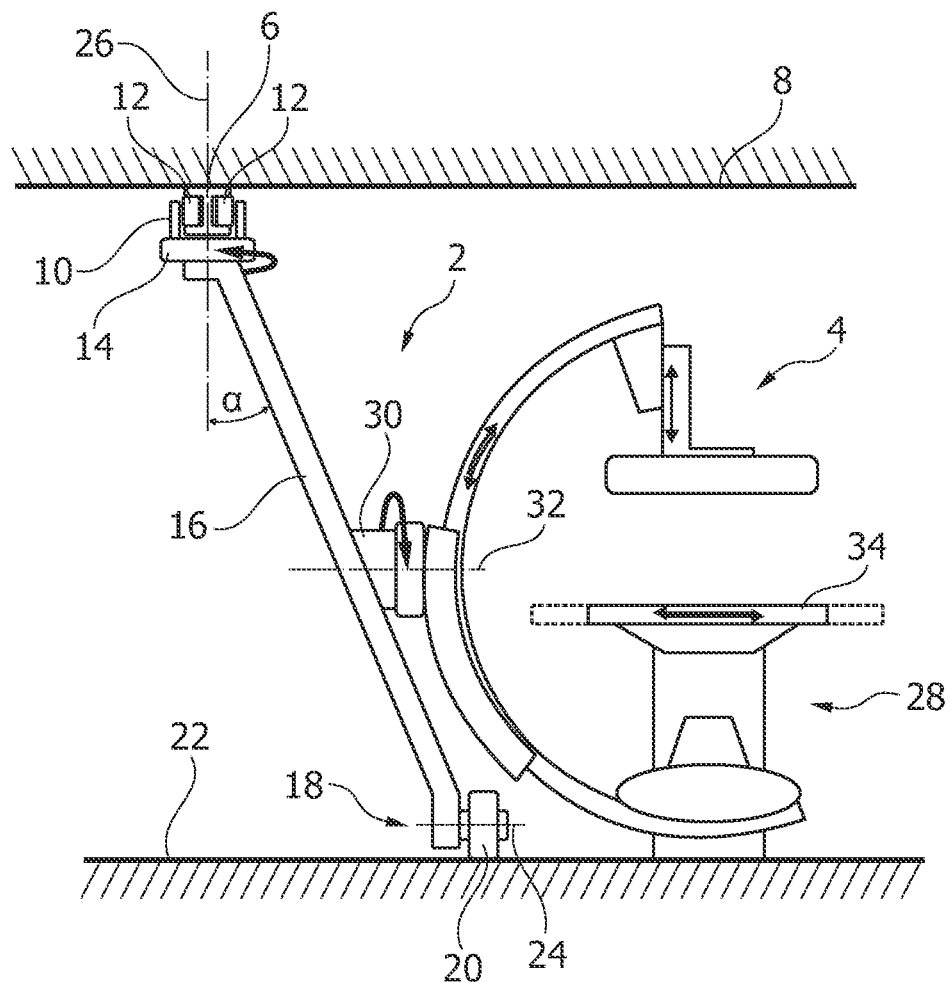
FIG. 1 shows an overview of a stand according to the present invention.

FIG. 1 shows a stand 2 for an X-ray examination apparatus realized as a C-arm 4 attached thereto. The stand 2 comprises a ceiling-rail 6 as a ceiling support assembly which is attached to a ceiling 8 of an operating room. The profile of the ceiling-rail 6 is chosen to a double-T-profile exemplarily. A carriage 10 comprising wheels 12 engages the ceiling-rail 6 and is thus able to move along a longitudinal extension of the ceiling-rail 6. Optionally, the carriage 10 includes a brake in order to block its motion relative to the ceiling-rail 6.

A pivot bearing 14 including an optional lock or locking mechanism is attached to the carriage 10. A holder 16 is attached to the bearing and extends to a ground support assembly 18 that exemplarily comprises a wheel 20 that runs on a ground 22 freely spinning around an axis 24 parallel to the ground 22. The ground support assembly 18 is positioned at one end of the holder 16 and provides a support for the weight of the C-arm 4 and is ideally positioned as close as possible underneath the center of gravity of the C-arm 4 plus the holder 12.

The ceiling-rail 6, the carriage 10 and the pivot bearing 14 are positioned at a lateral distance to the ground support assembly 18. Therefore, the holder 12 encloses an angle α greater than 0° with the pivot axis 26. Choosing the right angle α is a trade-off between desired or achievable stability of the stand 2 and the interference with the patient's area. With decreasing angle α the stability of the stand 2 decreases because the holder 16 can be tilted, bent or rotated relative to the ceiling-rail 6 and the carriage 10. If the angle α is rather large the stability of the stand 2 increases. With increasing angle α the interference with a patient's area increases in that the holder 16 occupies a large area inside the operating room. An angle α of about 10° to about 30° may be beneficial, but the invention shall not be limited to this angle range. Depending on the ceiling height, the weight of the C-arm, the size of the operating room and other factors the angle α can be further increased or decreased.

The pivot bearing 14 is realized in a manner that the holder 16 can be pivoted around a vertical axis 26 which is arranged perpendicular to the ceiling 8. This vertical axis 26 can also be referred to as pivot axis. By pivoting the holder 16 around the pivot axis 26 the wheel 20 of the ground support assembly 18 runs in a circle around the pivot axis 26 and thus moves the C-arm 4 away from a patient-support table 28. If the pivoting motion is far enough, the C-arm 4 is brought into a parking position where it does not disturb the area around the patient-support table 28.

The holder 16 comprises a mount 30 to which the C-arm 4 is attached. The mount 30 transfers the weight force of the C-arm 4 into the holder 16 where it is further distributed into the ground support assembly 18 and the ceiling-rail 6. The mount enables the C-arm 4 to be rotated around an axis 32 parallel to the ground 22 for adjusting the imaging angle of the C-arm 4. It is mandatory that the stand 2 is rigid and stable enough for the C-arm to be precisely positionable relative to the patient-support table 28. To enhance the positionability, the lie down area 34 of the patient-support table 28 can be moved laterally, to and forth from the holder 16.

Figure 2:
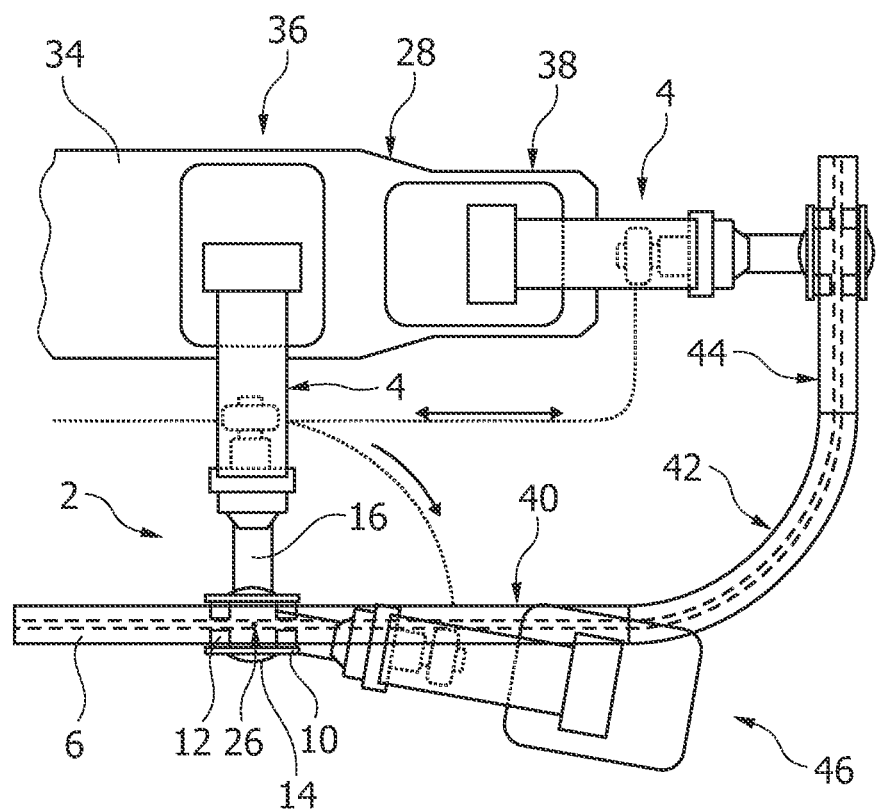
FIG. 2 shows a top-view of a stand according to the present invention.

FIG. 2 schematically shows how the stand 2 can be moved along the ceiling-rail 6 and how it can be brought into a parking position. In a first position 36 the C-arm 4 is held in a so-called "side position" relative to the patient-support table 28. From this side position the C-arm 4 can be moved further to a head-end or towards a foot-end. Thereby, the carriage 10 runs along a linear section 40 of the ceiling-rail 6. During the motion along the linear section 40 the C-arm is only moved parallel to a longitudinal side of the patient-support table 28.

For reaching a so-called "head-end position" 38 the ceiling-rail 6 also comprises a curved section 42 which is followed by another linear section 44 positioned perpendicular to the first linear section 40. Moving along the ceiling-rail 4 the carriage 10 reaches the curved section 42 and starts to turn relative to the patient-support table until it comes to the second linear section 44. There, the C-arm is positioned and is aligned perpendicular to a longitudinal side of the patient-support table 28 around a spot of the lie down area 34 on which the head of the patient rests during the operation.

For parking the C-arm 4 the stand 2 can be pivoted around the pivot axis 26 so that the C-arm 4 is moved far away from the patient-support table 28 in a parking position 46, where it does not obstruct the patient's area around the patient-support table 28.

Figure 3:
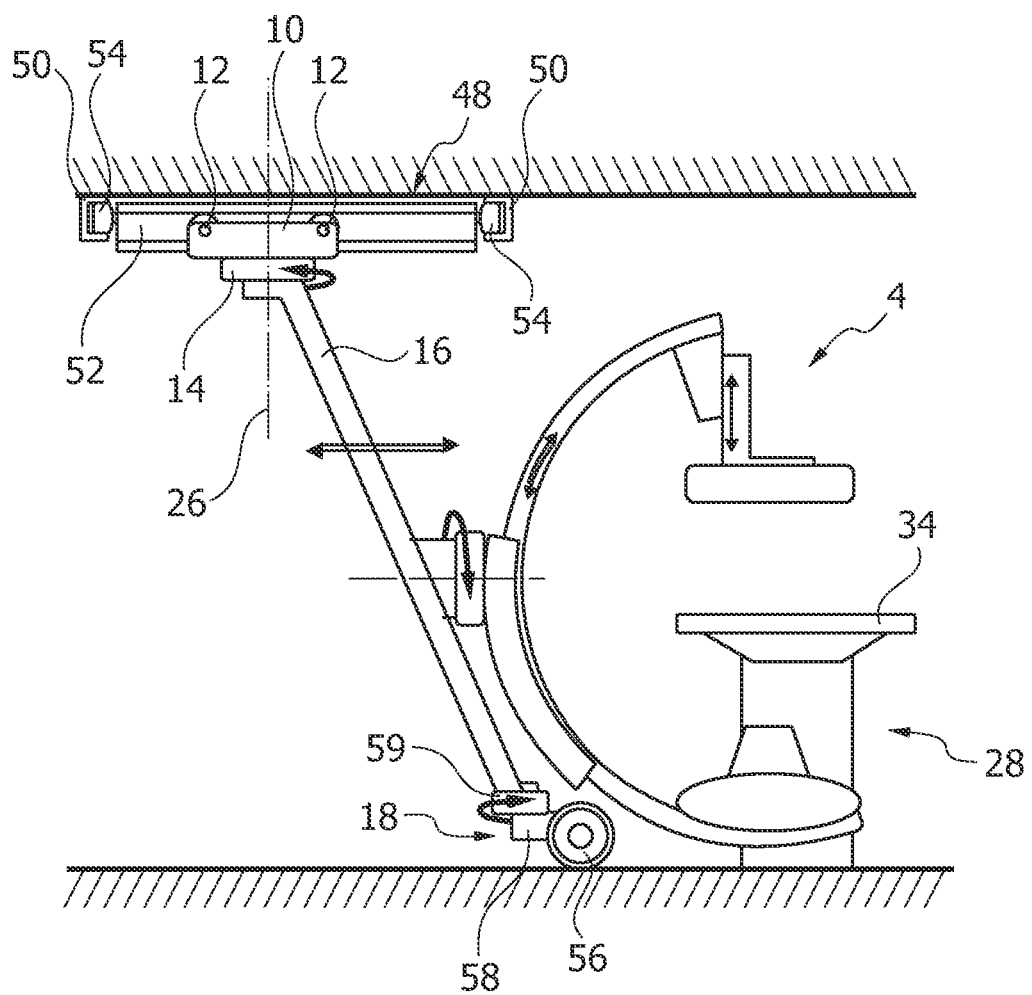
FIG. 3 shows an embodiment of a stand according to the present invention.

The embodiment in FIG. 3 an enhanced design of a stand 2 according to the invention. There, a ceiling-rail assembly 48 comprises two separate ceiling-rails 50 that exemplarily have a U-shaped profile. Between the ceiling-rails 50 a further rail 52 is situated that comprises wheels 54 running in the recesses of the ceiling rails 50. The further rail 52 is arranged perpendicular to the ceiling-rails 50 and enhances a longitudinal movement inside the ceiling-rails 50 by a lateral movement. A carriage 10 with wheels 12 is slidably supported in the rail 52 and also comprises a pivot bearing 14 to pivot the C-arm 4 around a vertical axis 26 into a parking position. Since the C-arm 4 can be accurately positioned using the ceiling-rail assembly 48 in two directions, a lateral movement of the lie-down-area 34 of the patient-support table 28 is not needed necessarily.

As a further modification, the ground support assembly 18 comprises two wheels 56 that are supported on a frame 58 which is mounted on a pivot bearing 59. This realizes "spin wheels" that allow a change of direction of motion easily. Thus, the degree of freedom in motion is enhanced and moving the C-arm 4 inside the operation room is eased.

Figure 4:
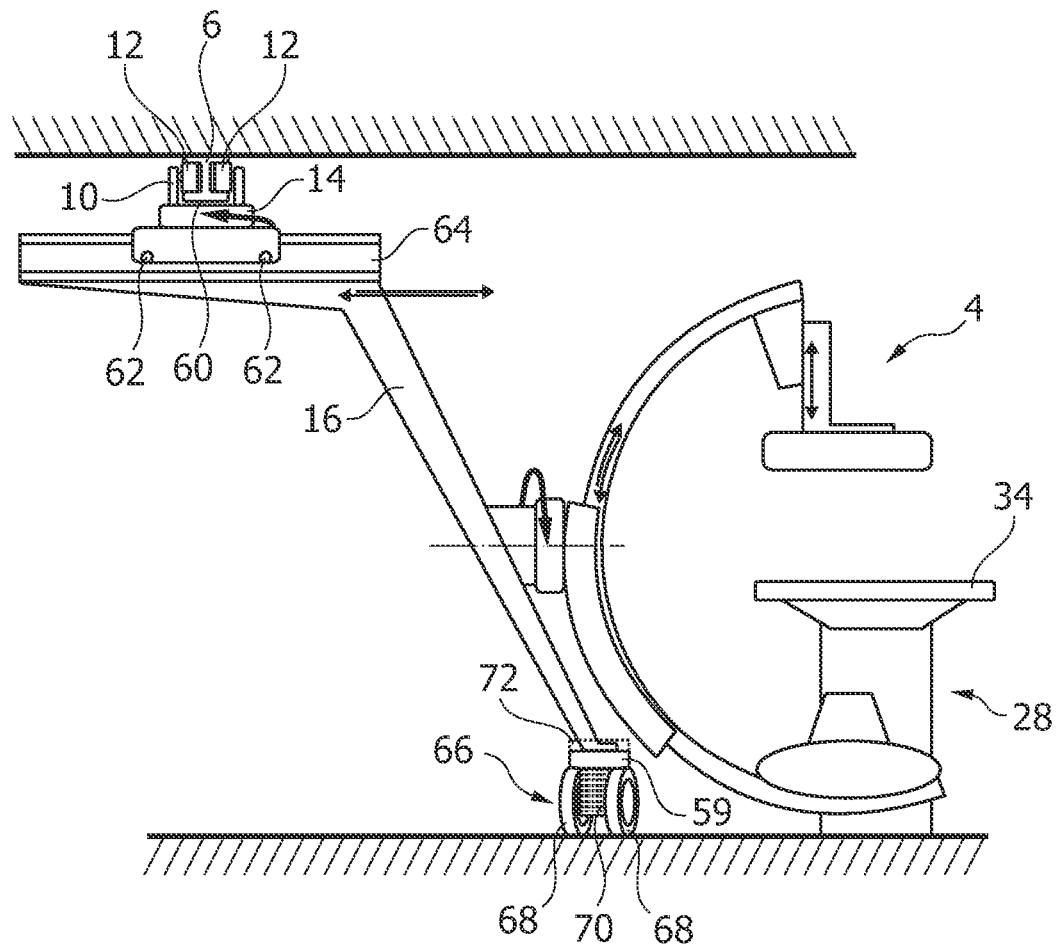
FIG. 4 shows an embodiment of a stand according to the present invention.

In FIG. 4 another modification of the stand 2 according to the invention is shown. In a ceiling-rail 6 a carriage 10 with wheels 12 is engaged and is able to be moved along the ceiling-rail 6. At the underside of the carriage 10 a pivot bearing 14 is situated on which a further carriage 60 with wheels 62 is attached. This further carriage 60 is engaged with a perpendicular ceiling-rail 64 that allows a lateral motion of the C-arm 4. Optionally, the carriage 60 includes a brake in order to block its motion relative to the ceiling-rail 64.

As an enhancement for this embodiment—which is also applicable for all previous embodiments—the ground support assembly 66 with wheels 68 comprises at least one motor 70 connected to the wheels 68 in order to support the motion of the C-arm 4 or fully automate the motion. For steering purposes preferably two motors 70 for driving independently rotating wheels 68 or for driving one wheel 68 and a further steering mechanism (72) are used.

Finally, it should be noted that the terms "comprising", "including", etc. do not exclude other elements or steps and the terms "a" or "an" do not exclude a plurality of elements. Also, elements described in association with different embodiments may be combined. It should also be noted that reference signs in the claims should not be construed as limiting the scope of the claims.

LIST OF REFERENCE SIGNS 2 stand
4 X-ray examination apparatus (C-arm)
6 ceiling-rail
8 ceiling
10 carriage
12 wheel
14 pivot bearing
16 holder
18 ground support assembly
20 wheel
22 ground
24 wheel axis
26 vertical axis
28 patient-support table
30 mount
32 axis
34 lie-down area
36 side-position
38 head-position
40 linear section of ceiling-rail
42 curved section of ceiling-rail
44 linear section of ceiling-rail
46 parking position
48 ceiling-rail assembly
50 ceiling-rail
52 rail
54 wheel
56 wheel
58 frame
59 pivot bearing
60 carriage
62 wheel
64 perpendicular rail
66 ground support assembly
68 wheel
70 motor

The invention claimed is:

1. A stand for an X-ray examination apparatus, comprising:
a movable ceiling support assembly for a ceiling of a room,
a ground support assembly for a floor of the room and
a holder extending from the ceiling support assembly to the ground support assembly,
wherein the ceiling support assembly is distanced laterally from the ground support assembly and
wherein the holder comprises a mount for holding the X-ray examination apparatus above the ground support assembly.

2. A stand according to claim 1, wherein the ceiling support assembly comprises a pivot bearing for pivoting the holder around a pivot axis vertical to a ceiling.

3. A stand according to claim 1, wherein the ceiling support assembly comprises at least one ceiling rail.

4. A stand according to claim 3, wherein the ceiling support assembly comprises at least one carriage supported by the at least one ceiling-rail.

5. A stand according to claim 1, wherein the ceiling support assembly comprises at least two ceiling-rails and at least two carriages supported by the ceiling-rails, wherein at least one of the ceiling-rails is positioned perpendicular to at least one remaining ceiling-rail.

6. A stand according to claim 1, wherein the ground support assembly comprises a pivot bearing.

7. A stand according to claim 1, wherein the ground support assembly comprises at least one wheel.

8. A stand according to claim 7, wherein the ground support assembly comprises two adjacent wheels.

9. A stand according to claim 7, wherein the ground support assembly comprises at least one motor to drive the at least one wheel.

10. A stand according to claim 8, wherein the ground support assembly comprises two motors to drive the two adjacent wheels independently or to drive one wheel and a further steering mechanism.

11. A stand according to claim 2, wherein ceiling support assembly comprises a lock to lock the pivot bearing of the ceiling support assembly in place.

12. A stand according to claim 1, wherein the ceiling support assembly comprises a brake to lock the ceiling support assembly in place.

13. A stand according to claim 1, wherein the holder is mounted firmly on the ceiling support assembly to not be tilted or turned relative to the ceiling support assembly.

14. An X-ray examination apparatus comprising a C-arm mounted on a stand comprising:
   a movable ceiling support assembly for a ceiling of a room,
   a ground support assembly for a floor of the room and
   a holder extending from the ceiling support assembly to the ground support assembly,
   wherein the ceiling support assembly is distanced laterally from the ground support assembly.

* * * * *